United States Patent [19]

Davison et al.

[11] Patent Number: 4,625,725

[45] Date of Patent: Dec. 2, 1986

[54] SURGICAL RASP AND METHOD OF MANUFACTURE

[75] Inventors: John A. Davison; Robert J. Kellar, both of San Jose, Calif.

[73] Assignee: Snowden-Pencer, Inc., Norcross, Ga.

[21] Appl. No.: 527,935

[22] Filed: Aug. 30, 1983

[51] Int. Cl.$^4$ ............................................. A61B 17/22
[52] U.S. Cl. .......................................... 128/304; 29/78
[58] Field of Search ....................... 128/304; 29/78, 79, 29/80

[56] References Cited

U.S. PATENT DOCUMENTS

| | | | |
|---|---|---|---|
| 1,032,897 | 7/1912 | Hamilton | 29/78 |
| 1,616,403 | 2/1927 | Womack | 29/78 |
| 1,725,686 | 8/1929 | Ufer | 29/78 |
| 2,082,685 | 6/1937 | Charlton | 29/78 |
| 2,089,619 | 8/1937 | Ripley | 29/78 |
| 2,455,348 | 12/1948 | Barstow | 76/101 |
| 2,898,914 | 8/1959 | Sardal | 128/304 |
| 3,016,771 | 1/1962 | Meissler et al. | 76/13 |
| 3,045,509 | 7/1962 | Severance et al. | 29/79 X |
| 3,509,611 | 5/1970 | Kifer | 29/78 |
| 3,605,527 | 9/1971 | Gambale | 76/101 |
| 3,640,280 | 2/1972 | Slanker et al. | 128/317 |
| 3,667,470 | 6/1972 | Rubin | 128/304 |
| 3,815,599 | 6/1974 | Deyerle | 128/305 |
| 4,182,204 | 1/1980 | Coon | 76/24 |

FOREIGN PATENT DOCUMENTS

| | | |
|---|---|---|
| 1295606 | 4/1961 | France . |
| 8300824 | 3/1983 | PCT Int'l Appl. . |
| 577391 | 5/1946 | United Kingdom . |
| 891403 | 5/1962 | United Kingdom . |

OTHER PUBLICATIONS

Medinisch–Orthopadische Technik, vol. 104, No 2, Marz.–Apr. 1984, p. 48, Stuttgart, DE; J. Eichler: "Uber eine neue Raspel zur Bearbeitung von Knochenspongiosa".

*Primary Examiner*—Hugh R. Chamblee
*Attorney, Agent, or Firm*—Jones & Askew

[57] ABSTRACT

A surgical rasp for scraping and reshaping bones, particularly useful in cosmetic surgery, comprises a handle and a rasp surfaced insert made from a tungsten carbide attached thereto. The tooth pattern of the rasped surface is created by cutting a plurality of substantially parallel grooves into the insert and subsequently cross cutting a plurality of substantially parallel grooves thereto. Further cross-cuts can be made depending on the particular tooth pattern desired. In a preferred embodiment, the teeth so formed have a trapezoidal-shaped face and a trapezoidal-shaped back which are coextensively integral to create a cutting edge. In an alternate preferred embodiment, the teeth so formed are shaped as three-sided truncated pyramids.

22 Claims, 10 Drawing Figures

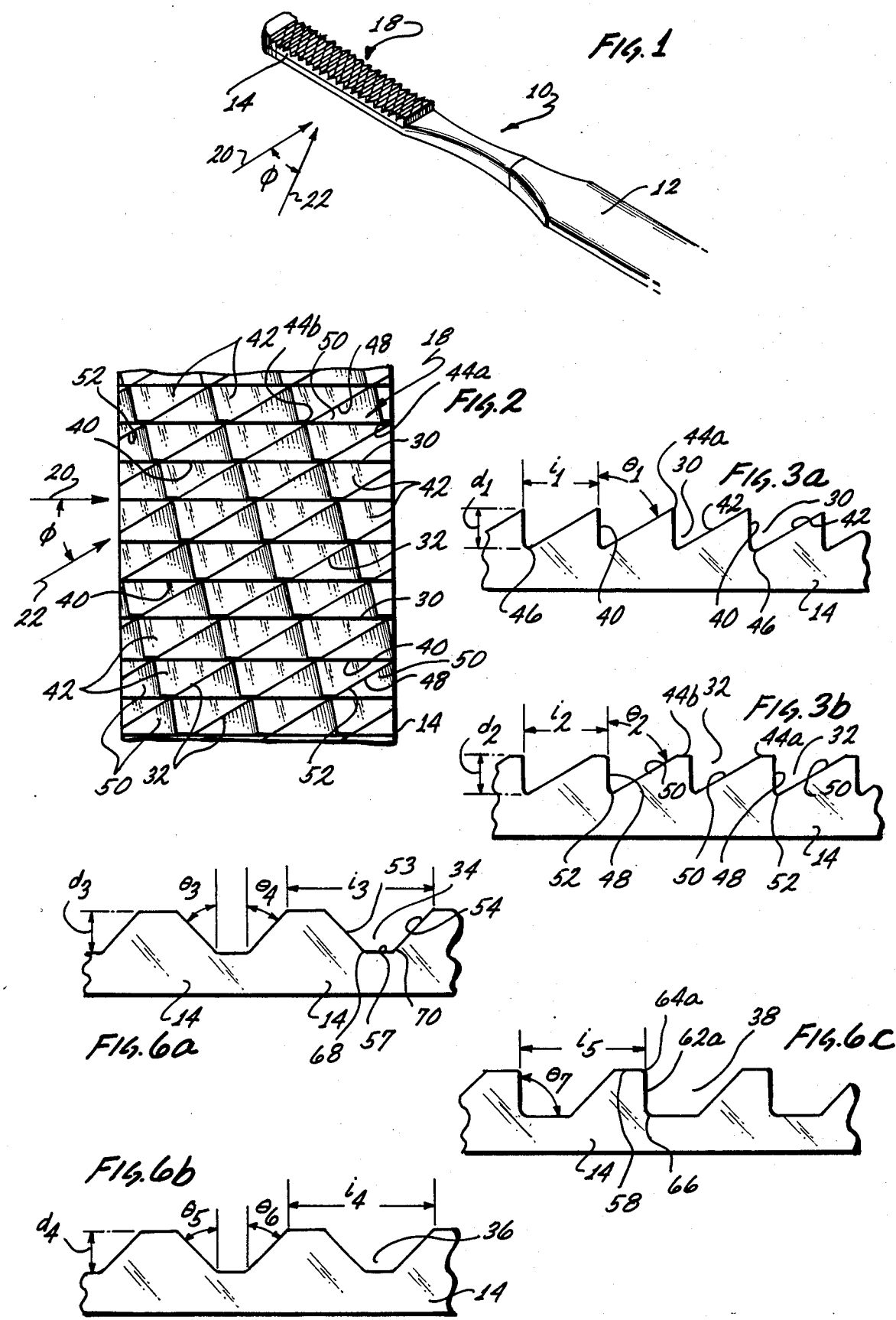

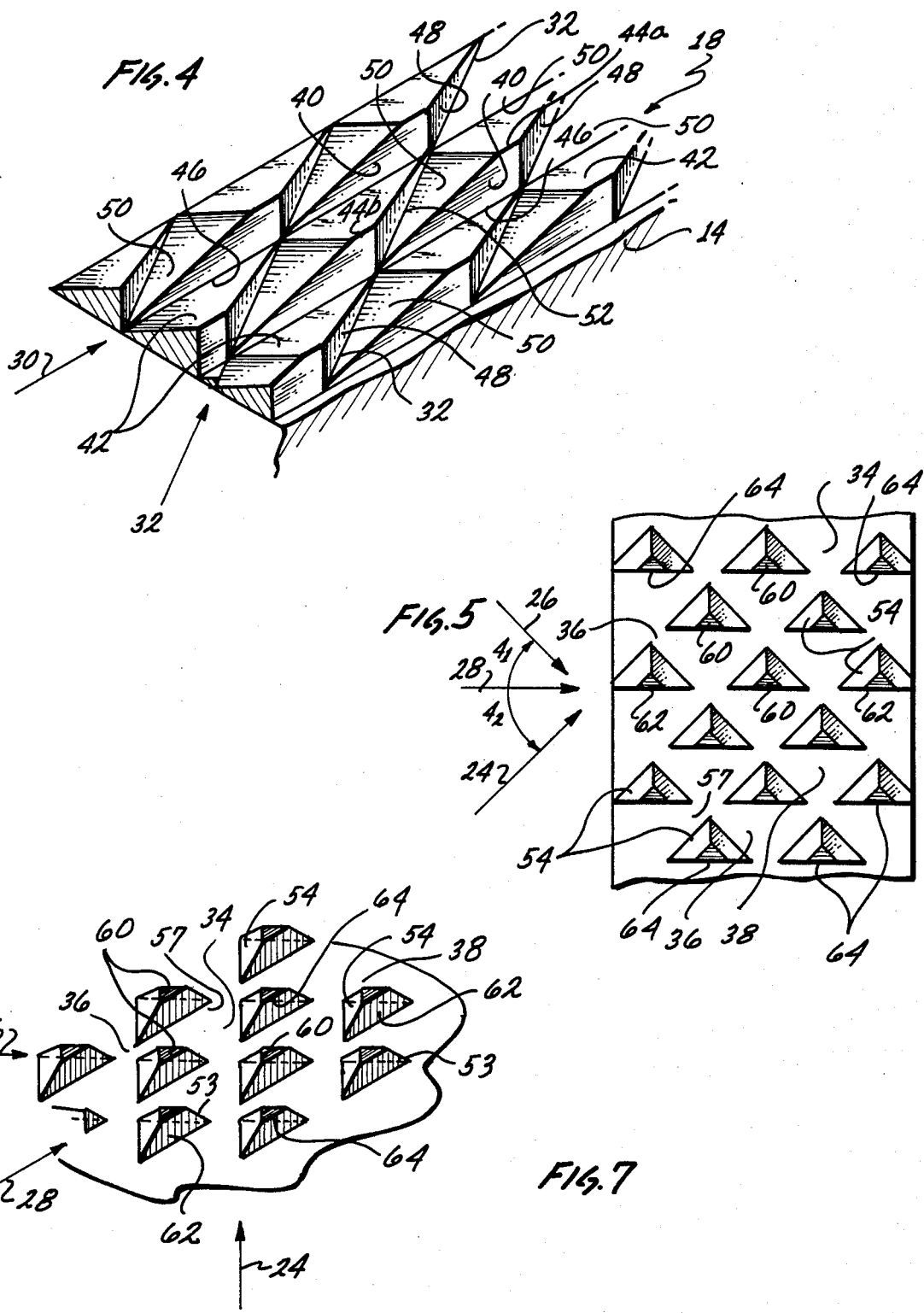

SURGICAL RASP AND METHOD OF MANUFACTURE

BACKGROUND OF THE INVENTION

This invention relates generally to a device used in the scraping and planing of an object for the purpose of reshaping and smoothing its surface. More particularly, the present invention relates to a surgical rasp useful in a variety of surgical applications. This invention is particularly, though not exclusively, useful in the removal, reshaping, and smoothing of bones for either prosthetic, cosmetic or facial surgery.

DESCRIPTION OF THE PRIOR ART

In surgical operations where it is necessary to remove or shape bony structures of the body, there is a recognized need for a rasp which operates effectively and leaves a relatively smooth surface that is not grooved or gouged. Not unexpectedly, satisfaction of these needs requires a surgical instrument having a precisely manufactured and well designed rasp surface. In the past, it has been necessary to use relatively soft metals in the manufacture of surgical rasps to obtain the particular tooth shape and tooth pattern that was desired for such surfaces. Soft metals, however, have some operational limitations. Specifically, rasps made from soft metals quickly dull. Because of the tendency for soft metal rasps to dull quickly, they are often discarded after only a few operations. Also, many of the present manufacturing practices introduce imperfections in the shape and alignment of individual teeth. In many instances, these imperfections have led to functional limitations such as grooving and gouging of the bony work surface. Further, in addition to the need for a durable and economical surgical rasp, there is the need for an instrument that is easily and quickly cleaned under circumstances, such as during surgery, when it may be necessary to use the same rasp repeatedly.

One example of a presently used method for manufacturing surgical rasps creates a scattered tooth pattern made by a plunge and pull back process. The result is the formation of teeth that are roughly in the shape of half pyramids. Though useful, close examination of the teeth so formed reveals the fact that the plunge and pull back process leaves uneven and pitted surfaces. During use of an insturment made by this method of manufacture, these pitted surfaces tend to accumulate and collect material more quickly than a smoother surface. Although any accumulation reduces the cutting effectiveness of the instrument, the more rapid the accumulation, the more frequently the instrument needs to be cleaned. Furthermore, during cleaning of the instrument, it is often difficult to dislodge accumulated material from the pits in the surfaces of the teeth. This difficulty is particularly troublesome if there is an immediate need for reuse of the instrument. Still another disadvantage of the plunge and pull back process is that it requires use of a relatively soft metal. As previously discussed, the resultant product is an instrument that becomes easily dulled and is generally discarded after only a few uses.

Several other processes for the manufacturing of rasp surfaces have been proposed. For example, a method of forming teeth on a metal strip by clamping the strip between the elements of a punch and the mated recesses of an anvil has been disclosed. Again, however, these processes have required use of softer metals and therefore they also produce instruments which have the disadvantages of being easily dulled and easily pitted. This makes them susceptible to collecting matter that reduces cutting efficiency. Furthermore, like the plunge and pull back process, these processes have not been shown to be effective in the manufacture of rasp surfaces from harder metals such as tungsten carbide. In fact, the difficulty in working with the harder metals has made the softer metals more preferable as a manufacturing material. Even when rasps have been manufactured with tungsten carbide, it has been necessary to form the teeth in soft carbide and then sinter the carbide to produce the desired hardness. Although this results in a rasp of sufficient hardness to overcome some of the problems solved by the present invention, sintering causes a shrinkage in the tungsten carbide that has a tendency to disadvantageously reduce the size and sharpness of the teeth.

One object of the present invention is to provide a surgical rasp which is configured to minimize grooving and gouging of the work surface during use of the rasp. Another object of this invention is to present a rasp surface that is easily cleaned in an operating room environment and returned to service in a minimum length of time. Still another object of the present invention is to provide a durable surgical rasp which can be used repetitively without undue dulling of the cutting surfaces of the rasp-type teeth. Yet another object of this invention is to present a rasp surface with an ability to withdraw debris from the work area.

SUMMARY OF THE INVENTION

A preferred embodiment of the invention includes an insert formed with rasp-type teeth which is attached to a handle. The insert is made of a hard metal, such as tungsten carbide, and the rasp-type teeth formed thereon have smooth sides for easy cleaning. Also, the teeth are aligned in a geometric pattern for planing a substantially smooth surface.

Manufacture of the preferred embodiments is accomplished by sawing a series of substantially parallel grooves into the surface of the insert with a diamond tipped saw that has a cutting edge configuration in the desired shape of the groove. A second series of substantially parallel grooves is then cross-cut into the insert to form the teeth and the desired tooth pattern. For some tooth patterns and shapes, it is possible that a third series of substantially parallel grooves needs to be cut transverse to both the first and second series of cuts. It should be appreciated that a variety of tooth patterns and tooth shapes can be formed onto the insert dependent only on the configuration of the saw's cutting edges, the number of cross cuts and the transverse angle of the subsequent cross cuts.

The novel features of this invention, as well as the invention itself, will be best understood from the accompanying drawings, taken together with the accompanying description, in which similar reference characters refer to similar parts, and in which:

BRIEF DESCRIPTION OF THE DRAWINGS

FIG. 1 is a perspective view of the surgical rasp;

FIG. 2 is a top plan view of a portion of the surgical rasp illustrating the cutting patterns for the preferred embodiment;

FIG. 3a is a side profile view of a portion of the rasp surface as seen in the direction of arrow 20 shown in FIG. 2;

FIG. 3b is a side profile view of a portion of the rasp surface as seen in the direction of arrow 22 shown in FIG. 2;

FIG. 4 is an enlarged perspective view of a portion of the rasp surface for the preferred embodiment;

FIG. 5 is a top plan view of a portion of the surgical rasp illustrating the cutting patterns of the alternate preferred embodiment;

FIG. 6a is a side profile view of a portion of the rasp surface as seen in the direction of arrow 24 shown in FIG. 5;

FIG. 6b is a side profile view of a portion of the rasp surface as seen in the direction of arrow 26 shown in FIG. 5;

FIG. 6c is a side profile view of a portion of the rasp surface as seen in the direction of arrow 28 shown in FIG. 5; and FIG. 7 is an enlarged perspective view of a portion of the rasp surface for the alternate preferred embodiment.

DESCRIPTION OF THE PREFERRED EMBODIMENTS

Referring now in detail to the drawings, the surgical rasp of the present invention is shown generally by the character 10 in FIG. 1. As shown in FIG. 1, the surgical rasp 10 is formed with a handle 12. Rigidly attached to the handle 12 by any means well known in the art, such as brazing, is an insert 14. The insert 14 is preferably made of a durable, wear-resistant material such as tungsten carbide. It should be appreciated, however, that any durable, wear-resistant metal is suitable for purposes of the present invention. For example, 440c mixed with vanadium carbide is another suitable material for use as an insert 14 for the surgical rasp 10 of the present invention.

In accordance with the present invention, a tooth pattern 18 is cut into the insert 14 prior to brazing or otherwise attaching the insert 14 to the handle 12. As can be appreciated by reference to FIG. 2 and FIG. 5, individual teeth on the cutting surface of the insert 14 are formed by a series of cross-cut grooves which form a geometric tooth pattern 18 on the insert 14.

In order to best understand the present invention, a general description of the necessary tools and the definition of terms which are used in the cutting of the grooves that make up the tooth pattern 18 is helpful. First, it must be appreciated that a saw (not shown) or some other tool which is capable of cutting or reshaping very hard metals is required. It has been determined that diamond tipped saws which are well known in the pertinent art are particularly suitable for the purposes of this invention. Next, it should be recognized that regardless of the tool used, it must have a cutting edge in the shape of the desired groove. The saw (not shown) configuration and the resultant geometry of each groove can be better appreciated by reference to FIG. 3a. For purposes of this initial discussion of groove geometry, subscripts will be omitted. In FIG. 3a, it can be seen that the cross-sectional geometry of any individual groove in the insert 14 is defined by at least three variables. The first variable, d, indicates the depth to which the saw (not shown) cuts into insert 14. The second variable, i, indicates the index or distance between corresponding points on the cutting paths of the saw in successive passes or cuts over the surface of the insert 14. Lastly, the groove angle $\theta$ is a general indication of the shape of the groove formed as the saw (not shown) cuts into the surface of the insert 14. It follows that the depth, d, is independent of the blade configuration of the cutting saw (not shown). On the other hand, the groove angle $\theta$ is dependent upon the particular shape and characteristics of the cutting saw (not shown) and the index, i, may be dependent on the blade width of the cutting saw (not shown).

Referring now to FIG. 2, it is seen that the preferred embodiment of the present invention is the result of a series of substantially parallel grooves cut in the direction of arrow 20 and substantially perpendicular to the longitudinal axis of the surgical rasp 10. The groove 30 is a result of this cut and is representative of other grooves cut into insert 14 in the direction of arrow 20. Referring now to FIG. 3a, it can be seen that the groove 30, in its cross-section, is generally a v-shaped groove having a face 40 substantially perpendicular to the surface of the rasp insert 14 and having an angled side 42 transverse thereto. Preferably, the intersection 46 between the face 40 and the side 42 has a smooth transitional interface of small radius of curvature, the purpose of which is to allow for easier cleaning of accumulated material from the intersection 46 than would be possible if the intersection 46 was sharply angled. In the preferred embodiment of the present invention, the depth $d_1$ for the groove 30 seen in FIG. 3a is approximately 0.028 inches. It should be appreciated, however, that the depth $d_1$ is actually a function of the desires for the particular instrument and can vary considerably from the dimension given for the preferred embodiment. Also in the preferred embodiment, the index $i_1$ would be on the order of 0.050 inches. Again, it should be appreciated that this is only representative of the preferred embodiment and that the index $i_1$ could take any range of values depending upon the desires for the particular instrument. Also in the preferred embodiment, the groove angle $\theta_1$ is preferably on the order of 60°. Again, depending on the particular tooth shape desired, a range of values for $\theta_1$ anywhere from 30° to 75° could be suitable. Referring again to FIG. 2, it is seen that a second series of cross cut parallel grooves is made on the insert 14 in the direction of arrow 22. Each cross-cut results in a groove such as the one represented by the refrence character 32. The cut angle $\phi$ between the direction of the first cut shown by directional arrow 20 and the direction of the cross cut shown by directional arrow 22 can take on any number of values. In the preferred embodiment, the cut angle $\phi$ would be on the order of 30°. However, as stated, the angle $\phi$ can vary and a range of values anywhere between 15° and 50° could result in a suitable configuration for the tooth pattern 18.

For a detailed description of individual grooves formed by the cross cut in the direction of arrow 22 of FIG. 2, of which groove 32 is only representative, reference is made to FIG. 3b. In FIG. 3b, it can be appreciated that the depth $d_2$ of groove 32 should preferably be the same as depth $d_1$ of groove 30. Also in the preferred embodiment, the groove angle $\theta_2$ shown in FIG. 3b is the same as the groove angle $\theta_1$ shown in FIG. 3a for the first cut and can be taken within the same range. This necessarily implies that the same cutting saw (not shown) can be used for both the first cut and the cross cut. The difference, however, between the first cut in the direction of arrow 20 in FIG. 2 and the cross cut in the direction of arrow 22 in FIG. 2 is in the index of the cut. For the cross cut in the direction of arrow 22, the index $i_2$ shown in FIG. 3b should be different from the index $i_1$ of the first cut in the direction of arrow 20. In the preferred embodiment, the index $i_2$ would be on the order of 0.054 inches. This difference of 0.004 inches between index $i_2$ and index $i_1$ results in a linear or elongated cutting edge for each tooth. The cutting edges 44a and 44b shown in FIG. 3b and FIG. 4 are only representative and are similar to the cutting edges of each tooth formed by the cutting process. It should be emphasized that the index $i_2$ of 0.054 inches is only representative. Indeed, index $i_2$ can take any value within a wide range. Its only limitation is that index $i_2$ must be greater than index $i_1$ in order to form the cutting edges.

Referring to FIG. 3b, it can be seen that the groove 32, like groove 30, is generally v-shaped and has a side 48 substantially perpendicular to the surface of the rasp insert 14 and has an angled side 50 transverse thereto. Again as with intersection 46, the intersection 52 between side 48 and side 50 preferably has a smooth transitional interface of small radius of curvature.

In accordance with the above description, cutting the series of substantially parallel grooves in the direction of arrow 20 and cross cutting the series of substantially parallel grooves in the direction of arrow 22 results in the formation of a geometrical pattern of teeth, a portion of which is shown in FIG. 4. More specifically, a pattern of teeth is formed, each of which has a leading face, such as leading face 40, that is trapezoidal in shape and which is substantially perpendicular to the surface of the insert 14. Oppositely disposed from the trapezoidal shaped face side 40 is a back side 42 which is also trapezoidal in shape but whose surface is transverse to the surface of insert 14. Between the face side 40 and back side 42 is a triangular shaped side 48 whose surface is substantially perpendicular to the surface of the insert 14. Oppositely disposed from side 48 is the triangular shaped side 50. Side 50, face side 40, side 48 and back side 42 together define the upper exposed surface of the cutting tooth. As can also be appreciated by reference to FIG. 4, each cutting tooth of the tooth pattern 18 has an elongated cutting edge, such as cutting edge 44a, which is formed at the juncture of face side 40 and back side 42.

The correlation between each individual tooth and the cutting grooves previously discussed can be appreciated by cross referencing between FIG. 4, FIG. 3a and FIG. 3b. In making this cross reference, it can be seen that the groove 30 forms the face side 40 of a trailing tooth and the back side 42 of a leading tooth and that the intersection 46 thus defines the juncture between the face side 40 of one tooth and the back side 42 of a separate tooth. It should also be appreciated that the groove 32 forms the triangular side 48 of one tooth and the triangular side 50 of the adjacent tooth and that the intersection 52 defines the juncture between the side 48 and the side 50. It can further be appreciated that the formation or cutting of substantially parallel grooves in the directions of arrow 20 and arrow 22, as above described, results in a precise tooth pattern, only a portion of which is shown in FIG. 4, and of which the groove 30 and the groove 32 are only representative.

Referring now to FIG. 5, it is seen that in the manufacture of the alternate preferred embodiment of the present invention, a series of substantially parallel grooves is first cut in the direction of arrow 24. The groove 34 is a result of this cut and is representative of other grooves cut into insert 14 in the direction of arrow 24. For a more detailed description of the groove 34, reference is made to FIG. 6a where it can be seen that the groove 34 in its cross-section is a generally trough-shaped groove having a bottom 57 substantially in the plane of the surface of the rasp insert 14. Further, the generally trough-shaped groove 34 has an angle side 54 transverse to the bottom 57 and an angled side 53 also transverse to the bottom 57. Preferably the intersection 70 between the side 54 and the bottom 57 and the intersection 68 between the side 53 and the bottom 57 each have a smooth transitional interface formed of small radius of curvature. Like the preferred embodiment, the purpose of these smooth transitions in the alternate preferred embodiment is to allow for easier cleaning of accumulated material from the intersections 68 and 70 than would be possible if they were sharply angled. In the alternate preferred embodiment of the present invention, the depth $d_3$ for the groove 34 as shown in FIG. 6a is aproximately 0.028 inches. It should be appreciated, however, that the depth $d_3$ is actually a function of the desires for the particular instrument and can vary considerably from the dimension given for the alternate preferred embodiment. Also, in the alternate preferred embodiment, the index $i_3$ should be on the order of 0.160 inches. Again, it should be appreciated that this is only representative of the preferred embodiment and that the index $i_3$ can take any range of values depending upon the desires for the particular instrument. Also in the alternate preferred embodiment, the groove angle $\theta_3$ and the groove angle $\theta_4$ are preferably on the order of 45°. Again, depending on the particular tooth shape desired, a range of values for groove angle $\theta_3$ and groove angle $\theta_4$ would be anywhere from 30° to 60°. Preferably, groove angle $\theta_3$ and groove angle $\theta_4$ are equal in order to give a symetrical cross section to the groove 34. It should be appreciated, however, that $\theta_3$ may differ from $\theta_4$ depending upon its desired shape for the particular tooth.

Referring again to FIG. 5, it is seen that a second series of parallel grooves are cut into the surface of the insert 14 in the direction of arrow 26. This second series of grooves is cross cut to the series of grooves previously described and which was represented by the groove 34. Each cross cut of this second series of grooves results in a groove such as the one represented by the reference character 36. The cut angle between the direction of the first cut which was shown by arrow 24 and the direction of the second series or cross cut shown by the arrow 26 can take on any number of values. As seen in FIG. 5, the angle between groove 36 and the groove 34 is the sum of the cut angle $\psi_1$ and the cut angle $\psi_2$. In the preferred alternate embodiment, the sum of cut angle $\psi_1$ and cut angle $\psi_2$ would be on the order of 90°. Also, the depth $d_4$ for the groove 36 would be substantially equivalent to the depth $d_3$ for the groove 34. Also, the groove angle $\theta_5$ and the groove angle $\theta_6$ for groove 36 would be substantially equivalent to the respective groove angle $\theta_3$ and groove angle $\theta_4$ of the groove 34. This necessarily implies that the same cutting saw (not shown) can be used for both the first cut and the cross cut. Thus, the second series of cuts or grooves taken in the direction of arrow 24 result in trough-shaped grooves such as the groove represented by character 36 which are substantially similar in all important respects to the previously described groove 34. Also, it should be appreciated that, for the cross cut in the direction of arrow 26, the index $i_4$ as shown in FIG. 6b should be the same as the index $i_3$ for the first cut which was taken in the direction of arrow 24. At this point in the manufacturing process, it can be appreciated that the result of these first two series of grooves is a four-sided pyramidal shaped tooth. It is important to note, however, that by choosing values for the groove angle $\theta$ and for the depth, d, it is possible that the result of the first two series of substantially parallel grooves in insert 14 will result in a truncated prism. Indeed, formation of teeth in the form of a truncated pyramid is preferable.

The alternate preferred embodiment requires a third series of substantially parallel grooves cut into the insert 14. Referring again to FIG. 5, it can be seen that the third series of grooves should be cut in the general direction indicated by the arrow 28. The groove indicated by the reference character 38 is representative of the grooves formed by this third series of cuts. Referring now to FIG. 6c, a side profile view of the groove 38 can be seen. The effect of this third series of cuts is to cut off half of the previously formed truncated pyramid. For this operation, it is necesary that the saw (not shown) have a profile which has a cutting edge shaped so that groove angle $\theta_7$, as shown in FIG. 6c, is substantially a right angle. Also, the saw (not shown) must be chosen so as to be narrow enough to cut off the front half of the pyramid without cutting into the back side of the pyramid-shaped teeth in the adjacent rows. The result is a groove, as shown in FIG. 6c, which has a side 62a that is substantially perpendicular to the surface of the insert 14. Also, as with the intersection of all other sides in the tooth pattern of the preferred embodiments, the intersection 66, shown in FIG. 6c, has a smooth transitional interface of small radius of curvature. Again, the purpose of this smooth transition is to allow for easier cleaning of the rasp 10 than would be possible if the intersections were sharply angled. Recognize that the index $i_5$ for the third series of cuts will be determined by how much of the previously formed pyramids it is desired to have removed. It has been found that with the index $i_3$ and index $i_4$ having values of 0.160 inches that an effective value for the index $i_5$ is 0.1131 inches. It must be emphasized, however, that all values given for the preferred embodiments are only representative. Indeed, the values for the depths $d_3$, $d_4$, and $d_5$; the indices $i_3$, $i_4$, and $i_5$; and the angle $\theta_3$, $\theta_4$, $\theta_5$, $\theta_6$, and $\theta_7$ can take on any in a range of values depending upon the desires of the particular tooth pattern to be formed.

In accordance with the above description, the cutting of three separate series of substantially parallel grooves respectively in the directions of the arrow 24, the arrow 26, and the arrow 28 results in the formation of a geometrical pattern of teeth, a portion of which is shown in FIG. 7. More specifically, a pattern of teeth is formed, each of which has a leading face, such as the face 62, which is integral with the side 54 and the side 55 to form a truncated pyramid having a top 60 and a cutting edge 64. As can be appreciated by reference to FIG. 7, the tooth described above is one of a series of substantially similar teeth which make up the tooth pattern 18 of the alternate preferred embodiment.

While the particular surgical rasp as herein shown and disclosed in detail is fully capable of obtaining the objects and providing the advantages herein before stated, it is to be understood that it is merely illustrative of the presently preferred embodiment of the invention and that no limitations are intended to the details of construction or design herein shown other than as defined in the appended claims.

We claim:
1. A surgical rasp comprising:
   a handle; and
   an insert rigidly attached to said handle having a surface formed with a plurality of generally v-shaped scraping grooves, each of said scraping grooves having a first side generally perpendicular to said surface and a second side transverse to said surface and spaced apart from each adjacent said scraping groove to form a sharp cutting edge therebetween, and a plurality of generally v-shaped diagonal grooves, cross-cut to said plurality of scraping grooves, each of said diagonal grooves having a first side generally perpendicular to said surface and a second side transverse to said surface and spaced apart from each adjacent said diagonal groove to provide for elongation of said sharp cutting edges.
2. A surgical rasp as cited in claim 1 wherein said plurality of scraping grooves are generally perpendicular to the longitudinal axis of said handle.
3. A surgical rasp as cited in claim 2 wherein said insert is made of a tungsten carbide.
4. A surgical rasp for scraping bones comprising:
   a handle; and
   an insert rigidly attached to said handle and having a surface formed with a plurality of solid substantially flat-sided cutting teeth wherein each of said teeth are formed with;
   a trapezoidal-shaped face side having a bottom margin
   integral with said insert and a top margin parallel to the bottom margin;
   a trapezoidal-shaped back side having a bottom margin
   generally parallel to the bottom margin of said face side and integral with said insert and having a top margin coextensively integral with the top margin of said face side to form a cutting edge.
5. A surgical rasp as cited in claim 4 wherein the projection of the top margin of said face side onto the bottom margin of said face side lies between the end points of the bottom margin of said face side.
6. The surgical rasp as cited in claim 5 wherein the projection of the top margin of said back side onto the bottom margin of said back side lies between the end points of the bottom margin of said back side.
7. The surgical rasp as cited in claim 6 wherein said face side is generally perpendicular to the surface of said insert.
8. The surgical rasp as cited in claim 7 wherein said cutting edges are in staggered overlapping alignment for smoothly scraping a surface,
9. The surgical rasp as cited in claim 8 wherein said cutting teeth and said insert are made of a tungsten carbide.
10. A surgical rasp for smoothing and shaping bones, comprising:
    a handle;
    a tungsten carbide insert rigidly attached to said handle;
    said insert having a plurality of substantially parallel generally V-shaped first grooves substantialy perpendicular to the longitudinal axis of said handle, said first grooves having a first groove angle and a first cut depth;

said insert having a plurality of substantially parallel generally V-shaped second grooves oriented at a predetermined cut angle with respect to said first grooves, said second grooves having a second groove angle and a second cut depth;

said first grooves and said second grooves forming a plurality of rasp teeth having a leading face substantially perpendicular to the surface of said insert, an oppositely disposed back side face transverse to the surface of said insert, a third side face substantially perpendicular to the surface of said insert, and a fourth side face.

11. The surgical rasp of claim 10, wherein said first cut depth and said second cut depth are about 0.028 inches.

12. The surgical rasp of claim 10, wherein said leading face and said back face are trapezoidal, and said third side face and said fourth side face are triangular.

13. The surgical rasp of claim 10, wherein each of said first grooves are spaced apart a predetermined first index distance, and each of said second grooves are spaced apart a predetermined second index distance.

14. The surgical rasp of claim 13, wherein said first index distance is different from said second index distance such that each of said rasp teeth have an elongated cutting edge.

15. The surgical rasp of claim 14, wherein said first index distance is about 0.050 inches and said second index distance is about 0.054 inches.

16. The surgical rasp of claim 10, wherein said first groove angle is between about 30 degrees and about 75 degrees.

17. The surgical rasp of claim 16, wherein said first groove angle is about 60 degrees.

18. The surgical rasp of claim 10, wherein said second groove angle is between about 30 degrees and about 75 degrees.

19. The surgical rasp of claim 18, wherein said second groove angle is about 60 degrees.

20. The surgical rasp of claim 10, wherein said cut angle is between about 15 degrees and about 50 degrees.

21. The surgical rasp of claim 20, wherein said cut angle is about 30 degrees.

22. A surgical rasp for smoothing and shaping bones, comprising:

a handle;

a tungsten carbide insert rigidly attached to said handle;

said insert having a plurality of substantially parallel generally v-shaped first grooves substantially perpendicular to the longitudinal axis of said handle;

said insert having a plurality of substantially parallel generally v-shaped second grooves oriented at a predetermined cut angle with respect to said first grooves;

said first grooves and said second grooves forming a plurality of rasp teeth having a leading face substantially perpendicular to the surface of said insert, an oppositely disposed back side face transverse to the surface of said insert, a third side face substantially perpendicular to the surface of said insert, and a fourth side face; and each of said first grooves spaced apart a predetermined first index distance, and each of said second grooves spaced apart a predetermine second index distance different from said first index distance such that each of said rasp teeth have an elongated cutting edge.

* * * * *